United States Patent [19]

Dorn

[11] 4,191,773

[45] Mar. 4, 1980

[54] SYNERGISTIC INSECTICIDAL COMPOSITION

[75] Inventor: Silvia Dorn, Dielsdorf, Switzerland

[73] Assignee: Hoffmann-La Roche Inc., Nutley, N.J.

[21] Appl. No.: 961,784

[22] Filed: Nov. 17, 1978

[30] Foreign Application Priority Data

Nov. 25, 1977 [CH] Switzerland .................. 14477/77

[51] Int. Cl.$^2$ ............................................. A01N 9/02
[52] U.S. Cl. ..................................... 424/282; 424/340
[58] Field of Search ............................... 424/282, 340

[56] References Cited

U.S. PATENT DOCUMENTS 3,362,871  1/1968  Fellig et al. ..................... 424/273

OTHER PUBLICATIONS

Chemical Abstracts, vol. 71 (1969), p. 38941m.

*Primary Examiner*—V. D. Turner
*Attorney, Agent, or Firm*—Jon S. Saxe; Bernard S. Leon; William M. Farley

[57] ABSTRACT

Insecticidal compositions, and methods for their use, which comprise a combination of 2,3-(isopropylidenedioxy)phenyl-methyl carbamate with 2-nitro-4-chlorophenyl 2-propynyl ether, a compound which synergizes the insecticidal activity of the carbamate.

5 Claims, No Drawings

SYNERGISTIC INSECTICIDAL COMPOSITION

BACKGROUND OF THE INVENTION

Phenyl carbamates are known insecticides as described, for example in German DOS. No. 1,910,259, German DOS No. 2,341,949, German DOS No. 1,922,929 and German DOS No. 2,311,384. British Pat. No. 1,220,056 and Pesticide Science 1972, 3, pp. 735–744 disclose 2,3-(isopropylidenedioxy)phenyl-methyl carbamate and its use as an insecticide. Further, U.S. patent application Ser. No. 826,503, filed Aug. 22, 1977, discloses a synergistic combination of 2,3-(isopropylidenedioxy)phenyl methyl [(trichloromethyl)-thio] carbamate with 2-nitro-4-chlorophenyl 2-propynyl ether. Synergistic insecticidal compositions containing a carbamate, e.g. 1-naphthyl-N-methyl carbamate and a propargyl ether, e.g. a trihalophenyl-2- propynyl ether are also disclosed in U.S. Pat. No. 3,362,871. However, there is no disclosure of insecticidal compositions containing a combination of 2,3-(isopropylidenedioxy)phenyl-methyl carbamate with 2-nitro-4-chlorophenyl 2-propynyl ether to synergize the insecticidal activity of the carbamate.

SUMMARY OF THE INVENTION

The insecticidal compositions of this invention contain, as an active ingredient, 2,3-(isopropylidenedioxy)-phenyl-methyl carbamate of the formula

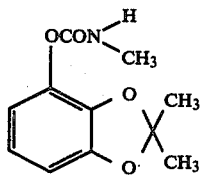

I and, as a synergist for its insecticidal activity, 2-nitro-4-chlorophenyl 2-propynyl ether, a compound of the formula

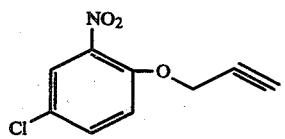

II

DETAILED DESCRIPTION OF THE INVENTION

This invention is directed to insecticidal compositions, and methods for their use which contain inert carrier material and, as the active component, 2,3-(isopropylidenedioxy)phenyl-methyl carbamate,

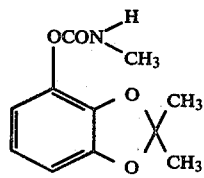

I and 2-nitro-4-chlorophenyl 2-propynyl ether,

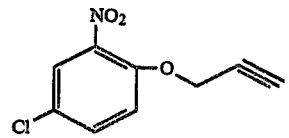

II

While the insecticidal activity of 2,3-(isopropylidenedioxy)phenyl-methyl carbamate is known, there is a substantial increase in its insecticidal activity where used in combination with the synergistic agent, 2-nitro-4-chlorophenyl 2-propynyl ether. This synergistic combination results in more rapid paralysis, more rapid and increased mortality of insects and effectiveness against heretofore resistant insect strains. This effectiveness against resistant strains of insects is believed due to the action of the propynyl ether in inhibiting enzymatic detoxification.

A particular advantage of the instant insecticidal compositions is that there is no increase the relatively low toxicity to warm-blooded animals and, especially, to mammals of the carbamate itself.

Further, the addition of the 2-nitro-4-chlorophenyl 2-propynyl ether to an insecticidal composition containing 2,3-(isopropylidenedioxy)phenyl-methyl carbamate increases the spectrum of insecticidal activity of the carbamate.

2,3-(Isopropylidenedioxy)phenyl-methyl carbamate has a long lasting activity against insects, e.g. the carbamate is effective against flies 7 to 14 days after application to a site. [See Pesticides Sciences 8, 177–182 (1977).]. However, using the insecticidal composition of this invention, a long lasting activity against insects of about six weeks is achieved. This has several practical effects since it eliminates frequent re-application of the insecticidal composition and minimizes pollution of the environment. These factors are of significance with the insecticidal compositions of this invention which have been developed for use both in the hygiene sectors and in the protection of stored products.

The relative proportions of the active components of the insecticidal compositions of the present invention can vary within rather wide limits depending on such factors as the intended use, the method of use, the insects to be controlled and the like. Conveniently 0.1–10 parts by weight of the synergistic compound is used with one part by weight of 2,3-(isopropylidenedioxy)-phenyl-methyl carbamate. A 1:1 weight ratio is preferred.

The concentration of the active ingredients in the ready-to-use insecticidal compositions depends again on such factors as the form in which the compositions are to be used and mode of use.

The insecticidal compositions can be used, together with carriers, as concentrates, granulates, sprays, aerosols or powders. For certain uses it is advantageous to use the compositions in the form of emulsions, suspensions or solutions containing emulsifying or wetting agents. Examples of materials suitable for use as solid carriers are, for example, chalk, talc, bentonite, kaolin, diatomaceous earth, siliceous earth, Fuller's earth, limestone, gypsum, powders and meals from organic waste products and the like.

In general, the insecticidal compositions of this invention can be prepared following the procedures described, for example, in Farm Chemicals, volume 128, page 52 et seq. The insecticidal compositions of this invention are prepared by mixing inert carrier material with the carbamate and the synergistic agent, 2-nitro-4-chlorophenyl 2-propynyl ether.

The instant insecticidal compositions can also contain other additives such as emulsifiers or masking agents and/or other known compounds having insecticidal activity. In addition, baits such as, for example, sugars and/or pheromones can also be added to the compositions.

The insecticidal compositions can be prepared as concentrates suitable for storage and transport. Such concentrates can contain, for example, 2–90% of the combination of active ingredients. This concentrate can be diluted, just prior to use, with the same or different carrier materials to provide the concentrations of active ingredients which are suitable for practical use.

A ready-to-use compositions can contain, for example, concentrations of active ingredients of 2–90 percent by weight. The concentration of active ingredients can be lower or higher, of course, depending on such factors as the method of use, the insects to be controlled and the like. Depending on the end uses, concentrations of active ingredients of from 2–8% or from 50–80% are especially preferred.

The insecticidal composition is active against a variety of insects in houses and stables, on animals, on plants, in the soil, on stored products and on materials.

The compositions containing the active ingredients are active against a wide variety of insects; for example, against Diptera, especially against the families Muscidae, Culicidae, Simuliidae, Tabanidae, Calliphoridae, Oestridae, Ceratopogonidae such as Musca spp., *Stomoxys calcitrans, Haematobia irritans;* Culex spp., Anopheles spp. and Aedes spp.; Simulium spp.; Tabanus spp.; *Cochliomyia hominivorax,* Lucilia spp. and Calliphora spp.; Hypoderma spp.; Culicoides spp.; Leptoconops spp.; against root maggot or Orthoptera, such as *Blattella germanica, Blatta orientalis, Periplaneta americana, Nauphoeta cinerea;* Lepidoptera such as *Plodia interpunctella, Esphestia kuehniella, Cadra cautella, Sitotroga cerealella, Laspeyresia pomonella, Lyonnetia clerkella;* Coleoptera such as *Sitophilus granarius, Sitophilus oryzae, Oryzaephilus surinamensis, Oryzephilus mercator, Tribolium confusum, Tribolium castaneum, Tribolium audax, Rhizopertha dominica,* Trogoderma variabile *Lasioderma serricorne, Popillia japonica, Atomaria linearis,* Diabrotica spp., cockchafer grubs; Hymenoptera such as ants, wasps or members of other orders such as cicadas, bugs, scale insects, silver fishs and fleas.

The present invention is also concerned with a method for providing a locus subject to or subjected to attack by insects free from such attack, which method comprises applying to said locus an effective amount of the insecticidal composition as defined hereinabove.

The preparation of 2,3-(isopropylidenedioxy)phenylmethyl carbamate (Bendiocarb) is described in British Pat. No. 1,220,056.

The preparation of 2-nitro-4-chlorophenyl 2-propynyl ether is described in U.S. Pat. No. 3,362,871.

The following Examples illustrate the insecticidal compositions and their activity against test insects.

The structural formulae and nomenclature of the compound of formulae I and II the synergistic compounds of formula II as well as commercial insecticides used in the Examples are listed below. For convenience, these compounds will be identified in the Examples by the corresponding numeral and tradenames listed below.

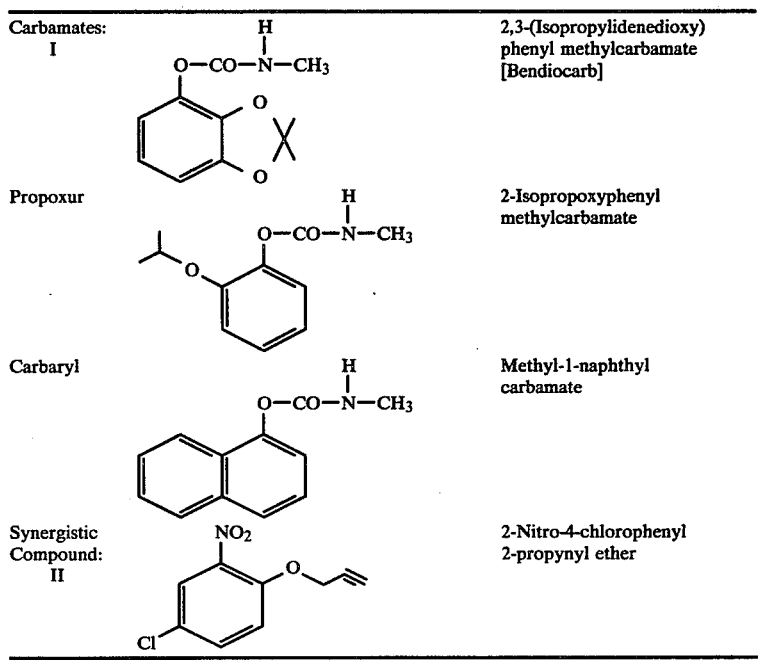

EXAMPLE 1

Petri dishes (diameter 90 mm) are treated with acetone solutions of one of the preparations listed in Table I. Ten 4–5 day old femal flies (*Musca domestica*, house fly) of a multiresistant strain are placed in each petri dish. Both untreated petri dishes and petri dishes treated with acetone are used as controls. The petri dishes are incubated at 25° C. and 60% relative humidity for 24 hours. The results, tabulated in Table I, are expressed as the percentage reduction in the survival rate of the flies in comparison to the controls (control mortality is 2%).

Table 1

| Active Ingredient | Dosage, µg/cm² | Synergist | Dosage, µg/cm² | % Reduction |
|---|---|---|---|---|
| I | 10 | II | 10 | 100 |
| I | 1 | II | 1 | 100 |
| I | 0.1 | II | 0.1 | 100 |
| I | 0.01 | II | 0.01 | 100 |
| I | 0.001 | II | 0.001 | 0 |
| I | 10 | — | — | 80 |
| I | 1 | — | — | 75 |
| I | 0.1 | — | — | 35 |
| I | 0.001 | — | — | 0 |
| Propoxur | 10 | II | 10 | 100 |
| Propoxur | 1 | II | 1 | 100 |
| Propoxur | 0.1 | II | 0.1 | 100 |
| Propoxur | 0.01 | II | 0.01 | 44 |
| Propoxur | 0.001 | II | 0.001 | 0 |
| Propoxur | 10 | — | — | 90 |
| Propoxur | 1 | — | — | 49 |
| Propoxur | 0.1 | — | — | 0 |
| — | — | II | 10 | 0 |
| — | — | II | 1 | 0 |

EXAMPLE 2

Filter paper discs (diameter 36 mm) are treated with an acetone solution of one of the following preparations.

| Active Ingredient | Synergist |
|---|---|
| I | II |
| Carbaryl | II |
| — | II |

Both untreated filter papers and filter papers treated with acetone alone are used as controls. The filter papers are placed in small plastic boxes. Ten freshly slipped cockroach larvae (*Blattella germanica*, German cockroach) are placed in each box. The boxes then incubated at 25° C. and 60% relative humidity for 14 days. The results, tabulated below in Table II are expressed as the percent reduction of the survival rate of the larvae in comparison to the controls (control mortality is 0%).

| Active Ingredient | Dosage, µg/cm² | Synergist | Dosage, µg/cm² | % Reduction |
|---|---|---|---|---|
| I | 10 | II | 10 | 100 |
| I | 1 | II | 1 | 95 |
| I | 0.1 | II | 0.1 | 0 |
| Carbaryl | 10 | II | 10 | 100 |
| Carbaryl | 1 | II | 1 | 0 |
| Carbaryl | 0.1 | II | 0.1 | 0 |
| — | — | II | 10 | 0 |
| — | — | II | 1 | 0 |

EXAMPLE 3

Petri dishes (diameter 90 mm) are treated with acetone solutions of one of the preparations listed in Table III. Twenty beetles (*Tribolium castaneum*, red flour beetle) are placed in each petri dish. Both untreated petri dishes and petri dishes treated with acetone are used as controls. The petri dishes are incubated at 25° C. and 60% relative humidity for 48 hours. The results, tabulated in Table III are expressed as the percentage reduction in the survival rate of the beetle in comparison to the controls (control mortality is 2%.

Table III

| Active Ingredient | Dosage, g/cm² | Synergist | Dosage, g/cm² | % Reduction |
|---|---|---|---|---|
| I | 1 | II | 1 | 100 |
| I | 0.1 | II | 0.1 | 100 |
| I | 0.01 | II | 0.01 | 5 |
| I | 1 | — | — | 70 |
| I | 0.1 | — | — | 55 |
| I | 0.01 | — | — | 0 |
| — | — | II | 10 | 0 |

EXAMPLE 4

This Example illustrates the persistence of an insecticidal composition of this invention when applied to the surfaces of an animal shed.

The following formulation is prepared with all ingredients reported as percents by weight based on the weight of the total composition.

Formulation A

| Ingredient | % |
|---|---|
| Active ingredient and/or Synergist | 50 |
| Silcasil S (hydrated silica, about 87% $SiO_2$) | 5.0 |
| Kaolin B 24 (mainly $Al_2 Si_2 O_5(OH)_4$) | 42.0 |
| Tensiofix BCZ (sodium lauryl sulfate) | 1.0 |
| Tensiofix LX special (sodium lignosulfonate) | 2.0 |

The active ingredient and/or synergist are mixed with the other ingredients in a spray tank. The walls, ceilings and supports of the shed are sprayed with a spray of the resulting powder. About 6 square meters are sprayed for each large animal unit. [A large animal unit (LAU) is defined as 1 cow or 6 calves.]

Sufficient granulated sugar is added to Formulation A to provide 5 grams of this bait per square meter of sprayed surface.

The test insect used was *Musca domestica*, house fly (open air strain).

To evaluate the effectiveness of the insecticide compositions, the numbers of flies per large animal unit (flies/LAU) are determined at 14, 28 and 56 days after spraying the sheds. These results are tabulated in Table IV.

Before spray treatment of the sheds the flies/LAU averaged about 30. The limit of tolerable molestation is regarded as 15 flies LAU.

Table IV

| Active Ingredient | Spray Dosage,g of a.i./m² | Synergist(s) | Spray Dosage,g of S/m² | Flies/LAU Days after treatment 14 | 28 | 56 |
|---|---|---|---|---|---|---|
| I | 1 | II | 1 | 1 | 2 | 11 |
| I | 1 | — | — | 22 | >30 | >30 |
| Carbaryl | 1 | II | 1 | 18 | >30 | >30 |

Neither the synergist alone nor the combination of carbaryl with the synergist is as effective as a long-term insecticide as the insecticidal composition of this invention.

I claim:
1. An insecticidal composition comprising inert carrier material and, as the active component, an amount of the combination of 2,3-(isopropylidenedioxy)phenyl-methyl carbamate and 2-nitro-4-chlorophenyl 2-propynyl ether which is effective as an insecticide and wherein the active component comprises from about 0.1 to about 10 parts by weight of 2-nitro-4-chlorophenyl 2-propynyl ether to one part by weight of 2,3-(isopropylidenedioxy)phenyl-methyl carbamate.

2. The insecticidal composition of claim 1 wherein the weight ratio of 2-nitro-4-chlorophenyl 2-propynyl ether to 2,3-(isopropylidenedioxy)phenyl-methyl carbamate is 1:1.

3. The insecticidal composition of claim 1 wherein the active component is from about 2 percent by weight to about 90 percent by weight based on the total weight of the composition.

4. A method of killing insects which comprises contacting the insects with an insecticidally effective amount of the composition of claim 1.

5. A method for providing a locus subject to or subjected to attack by insects free from such attack which comprises applying to said locus an insecticidally effective amount of the composition of claim 1.

* * * * *